United States Patent [19]

Alikhan

[11] Patent Number: 5,667,625
[45] Date of Patent: *Sep. 16, 1997

[54] APPARATUS FOR FORMING A FIBROUS LAMINATED MATERIAL

[75] Inventor: Mir Inayeth Alikhan, Marietta, Ga.

[73] Assignee: Kimberly-Clark Worldwide, Inc., Irving, Tex.

[*] Notice: The term of this patent shall not extend beyond the expiration date of Pat. No. 5,580,418.

[21] Appl. No.: 626,575

[22] Filed: Apr. 2, 1996

Related U.S. Application Data

[63] Continuation of Ser. No. 353,581, Dec. 12, 1994, abandoned, which is a continuation of Ser. No. 973,146, Nov. 6, 1992, abandoned.

[51] Int. Cl.$^6$ ........................................ B32B 31/04
[52] U.S. Cl. .................. 156/553; 156/209; 156/252; 156/253; 156/269; 156/290; 156/459; 156/543; 156/555
[58] Field of Search ........................... 156/209, 252, 156/253, 553, 290, 554, 555, 581, 154, 269, 324, 459, 543

[56] References Cited

U.S. PATENT DOCUMENTS

| | | |
|---|---|---|
| D. 239,137 | 3/1976 | Appleman . |
| D. 259,219 | 5/1981 | Bates . |
| D. 311,997 | 11/1990 | Legare . |
| D. 313,319 | 1/1991 | Legare . |
| D. 313,512 | 1/1991 | Legare . |
| D. 314,672 | 2/1991 | Legare . |
| D. 314,673 | 2/1991 | Legare . |
| 3,024,154 | 3/1962 | Singleton et al. . |
| 3,292,619 | 12/1966 | Egler . |
| 3,307,961 | 3/1967 | Stiehl et al. . |
| 3,441,021 | 4/1969 | Endres . |
| 3,459,618 | 8/1969 | Egler . |
| 3,507,943 | 4/1970 | Such et al. . |
| 3,508,991 | 4/1970 | Yunan ........................... 156/209 |
| 3,542,634 | 11/1970 | Such et al. . |
| 3,676,242 | 7/1972 | Prentice . |
| 3,765,974 | 10/1973 | Petersik et al. ................ 156/209 X |
| 3,811,979 | 5/1974 | Dempsey et al. . |
| 3,888,254 | 6/1975 | Hendricks . |
| 3,945,386 | 3/1976 | Anczurowski . |
| 3,949,127 | 4/1976 | Ostermeier . |

(List continued on next page.)

FOREIGN PATENT DOCUMENTS

| | | |
|---|---|---|
| 1 086 627 | 9/1980 | Canada . |
| 2009807 | 8/1991 | Canada . |
| 1288584 | 9/1991 | Canada . |
| 0 006 264 | 1/1980 | European Pat. Off. . |
| 0 010 439 | 4/1980 | European Pat. Off. . |
| 0 019 754 | 12/1980 | European Pat. Off. . |
| 0 040 447 | 11/1981 | European Pat. Off. . |
| 0 039 973 | 11/1981 | European Pat. Off. . |
| 0 039 974 | 11/1981 | European Pat. Off. . |
| 0 040 084 | 11/1981 | European Pat. Off. . |
| 0 006 647 | 7/1983 | European Pat. Off. . |
| 0 158 490 | 10/1985 | European Pat. Off. . |
| 0 160 569 | 11/1985 | European Pat. Off. . |
| 0164740A3 | 12/1985 | European Pat. Off. . |
| 0 172 420 | 2/1986 | European Pat. Off. . |
| 0 176 914 | 4/1986 | European Pat. Off. . |

(List continued on next page.)

Primary Examiner—Jeff H. Aftergut
Attorney, Agent, or Firm—Nicholas N. Leach; James B. Robinson

[57] ABSTRACT

This invention relates to a fibrous laminated material wherein a first fibrous layer comprising a plurality of staple fibers or continuous filaments of a thermoplastic material and a second fibrous layer comprising a plurality of staple fibers or continuous filaments of two or more thermoplastic or other materials are bonded together in a spaced apart bonding pattern having apertures formed therein to form a fibrous laminate having improved liquid distribution and management properties as well as enhanced comfort and softness when placed in contact with human skin. Also disclosed are a method and apparatus for making such a fibrous laminate.

12 Claims, 7 Drawing Sheets

U.S. PATENT DOCUMENTS

| | | |
|---|---|---|
| 3,953,638 | 4/1976 | Kemp . |
| 3,965,906 | 6/1976 | Karami . |
| 3,967,623 | 7/1976 | Butterworth . |
| 3,994,299 | 11/1976 | Karami . |
| 4,014,341 | 3/1977 | Karami . |
| 4,035,219 | 7/1977 | Cumbers . |
| 4,039,711 | 8/1977 | Newman . |
| 4,041,203 | 8/1977 | Brock et al. . |
| 4,073,991 | 2/1978 | Focht . |
| 4,088,726 | 5/1978 | Cumbers . |
| 4,128,679 | 12/1978 | Pohland . |
| 4,209,563 | 6/1980 | Sisson ............................... 156/167 X |
| 4,216,772 | 8/1980 | Tsuchiya et al. . |
| 4,285,342 | 8/1981 | Mesek . |
| 4,296,168 | 10/1981 | Ambrose . |
| 4,323,069 | 4/1982 | Ahr et al. . |
| 4,324,246 | 4/1982 | Mullane et al. . |
| 4,333,465 | 6/1982 | Wiegner . |
| 4,333,979 | 6/1982 | Sciaraffa et al. . |
| 4,377,615 | 3/1983 | Suzuki et al. . |
| 4,379,198 | 4/1983 | Jaeschke et al. . |
| 4,392,862 | 7/1983 | Marsan et al. . |
| 4,397,644 | 8/1983 | Matthews et al. . |
| 4,417,893 | 11/1983 | Mizutani et al. . |
| 4,451,520 | 5/1984 | Tecl et al. . |
| 4,469,734 | 9/1984 | Minto et al. . |
| 4,480,000 | 10/1984 | Watanabe et al. . |
| 4,488,928 | 12/1984 | Ali Khan et al. . |
| 4,518,451 | 5/1985 | Luceri et al. . |
| 4,519,799 | 5/1985 | Sakurai et al. . |
| 4,522,203 | 6/1985 | Mays . |
| 4,560,372 | 12/1985 | Pieniak . |
| 4,568,581 | 2/1986 | Peoples, Jr. . |
| 4,578,069 | 3/1986 | Whitehead et al. . |
| 4,588,630 | 5/1986 | Shimalla . |
| 4,592,943 | 6/1986 | Cancian et al. . |
| 4,610,352 | 9/1986 | Howey et al. . |
| 4,626,254 | 12/1986 | Widlund et al. . |
| 4,627,848 | 12/1986 | Lassen et al. . |
| 4,629,457 | 12/1986 | Ness . |
| 4,634,440 | 1/1987 | Widlund et al. . |
| 4,650,481 | 3/1987 | O'Connor et al. . |
| 4,652,484 | 3/1987 | Shiba et al. . |
| 4,667,665 | 5/1987 | Blanco et al. . |
| 4,675,013 | 6/1987 | Ruffo . |
| 4,681,793 | 7/1987 | Linman et al. . |
| 4,690,679 | 9/1987 | Mattingly, III . |
| 4,710,186 | 12/1987 | DeRossett et al. . |
| 4,725,473 | 2/1988 | Van Gompel et al. . |
| 4,726,976 | 2/1988 | Karami et al. ...................... 156/253 X |
| 4,737,404 | 4/1988 | Jackson . |
| 4,755,413 | 7/1988 | Morris . |
| 4,761,322 | 8/1988 | Raley . |
| 4,762,520 | 8/1988 | Wallstrom . |
| 4,770,657 | 9/1988 | Ellis et al. . |
| 4,778,460 | 10/1988 | Braun et al. . |
| 4,781,710 | 11/1988 | Megison et al. . |
| 4,781,962 | 11/1988 | Zamarripa et al. . |
| 4,783,231 | 11/1988 | Raley ..................................... 156/167 |
| 4,787,947 | 11/1988 | Mays . |
| 4,794,034 | 12/1988 | Nishizawa et al. . |
| 4,798,603 | 1/1989 | Meyer et al. . |
| 4,798,604 | 1/1989 | Carter . |
| 4,804,378 | 2/1989 | Shiba et al. . |
| 4,806,411 | 2/1989 | Mattingly, III . |
| 4,844,965 | 7/1989 | Foxman . |
| 4,847,134 | 7/1989 | Fahrenkrug . |
| 4,850,990 | 7/1989 | Huntoon et al. . |
| 4,854,984 | 8/1989 | Ball et al. ............................ 156/553 X |
| 4,857,065 | 8/1989 | Seal . |
| 4,863,785 | 9/1989 | Berman et al. . |
| 4,878,974 | 11/1989 | Kagawa . |
| 4,882,213 | 11/1989 | Gaddis et al. . |
| 4,886,697 | 12/1989 | Perdelwitz, Jr. . |
| 4,891,258 | 1/1990 | Fahrenkrug . |
| 4,892,535 | 1/1990 | Bjornberg et al. . |
| 4,908,026 | 3/1990 | Sukiennik et al. . |
| 4,929,303 | 5/1990 | Sheth . |
| 4,994,053 | 2/1991 | Lang . |
| 4,995,930 | 2/1991 | Merz et al. . |
| 5,009,651 | 4/1991 | Kamishioiri . |
| 5,030,229 | 7/1991 | Yang . |
| 5,078,710 | 1/1992 | Suda et al. . |
| 5,114,787 | 5/1992 | Chaplin et al. . |
| 5,137,600 | 8/1992 | Barnes et al. . |
| 5,151,091 | 9/1992 | Glaug et al. . |
| 5,171,238 | 12/1992 | Kajander . |

FOREIGN PATENT DOCUMENTS

| | | |
|---|---|---|
| 0 053 928 | 5/1986 | European Pat. Off. . |
| 0 203 821 | 12/1986 | European Pat. Off. . |
| 0 203 823 | 12/1986 | European Pat. Off. . |
| 0 205 286 | 12/1986 | European Pat. Off. . |
| 0 214 608 | 3/1987 | European Pat. Off. . |
| 0 217 032 | 4/1987 | European Pat. Off. . |
| 0 219 978 | 4/1987 | European Pat. Off. . |
| 0 252 041 | 1/1988 | European Pat. Off. . |
| 0 257 280 | 3/1988 | European Pat. Off. . |
| 0 260 131 | 3/1988 | European Pat. Off. . |
| 0 262 817 | 4/1988 | European Pat. Off. . |
| 0 286 409 | 10/1988 | European Pat. Off. . |
| 0 140 560 | 11/1988 | European Pat. Off. . |
| 0 293 482 | 12/1988 | European Pat. Off. . |
| 0 294 178 | 12/1988 | European Pat. Off. . |
| 0 297 411 | 1/1989 | European Pat. Off. . |
| 0 307 116 | 3/1989 | European Pat. Off. . |
| 0 309 073 | 3/1989 | European Pat. Off. . |
| 0 319 222 | 6/1989 | European Pat. Off. . |
| 0 140 470 | 9/1989 | European Pat. Off. . |
| 0 235 309 | 10/1989 | European Pat. Off. . |
| 0 336 578 | 10/1989 | European Pat. Off. . |
| 0 139 484 | 11/1989 | European Pat. Off. . |
| 0 173 058 | 3/1990 | European Pat. Off. . |
| 0 358 031 | 3/1990 | European Pat. Off. . |
| 0 360 929 | 4/1990 | European Pat. Off. . |
| 0 367 989 | 5/1990 | European Pat. Off. . |
| 0 370 835 | 5/1990 | European Pat. Off. . |
| 0 207 904 | 6/1990 | European Pat. Off. . |
| 0 372 363 | 6/1990 | European Pat. Off. . |
| 0 391 661 | 10/1990 | European Pat. Off. . |
| 0 395 381 | 10/1990 | European Pat. Off. . |
| 0 396 108 | 11/1990 | European Pat. Off. . |
| 0 403 187 | 12/1990 | European Pat. Off. . |
| 0 420 256 | 4/1991 | European Pat. Off. . |
| 0 421 649 | 4/1991 | European Pat. Off. . |
| 0 422 504 | 4/1991 | European Pat. Off. . |
| 0 423 049 | 4/1991 | European Pat. Off. . |
| 0 127 851 | 7/1991 | European Pat. Off. . |
| 0 238 334 | 8/1991 | European Pat. Off. . |
| 0 245 074 | 9/1991 | European Pat. Off. . |
| 0 257 280 | 9/1991 | European Pat. Off. . |
| 0 444 671 | 9/1991 | European Pat. Off. . |
| 0 242 766 | 3/1992 | European Pat. Off. . |
| 0 482 918 | 4/1992 | European Pat. Off. . |
| 0 489 205 | 6/1992 | European Pat. Off. . |
| 0 492 554 | 7/1992 | European Pat. Off. . |
| 0 495 212 | 7/1992 | European Pat. Off. . |
| 0 505 027 | 9/1992 | European Pat. Off. . |
| 0 523 683 | 1/1993 | European Pat. Off. . |
| 0 539 703 | 5/1993 | European Pat. Off. . |
| 0596191A1 | 5/1994 | European Pat. Off. . |
| 0596532A1 | 5/1994 | European Pat. Off. . |

| | | | | | | |
|---|---|---|---|---|---|---|
| 2 215 178 | 9/1974 | France . | | 2 014 046 | 8/1979 | United Kingdom . |
| 2 455 884 | 1/1981 | France . | | 2 028 567 | 3/1980 | United Kingdom . |
| 2 473 304 | 8/1984 | France . | | 1 574 498 | 9/1980 | United Kingdom . |
| 2 617 682 | 1/1989 | France . | | 2 047 619 | 12/1980 | United Kingdom . |
| 2 617 683 | 1/1989 | France . | | 2 000 079 | 1/1982 | United Kingdom . |
| 2 204 855 | 8/1973 | Germany . | | 2 023 494 | 9/1982 | United Kingdom . |
| 26 14 160 | 10/1977 | Germany . | | 2 023 068 | 11/1982 | United Kingdom . |
| 29 25 090 | 1/1980 | Germany . | | 2 055 690 | 5/1983 | United Kingdom . |
| 31 38 852 | 4/1983 | Germany . | | 2 124 907 | 2/1984 | United Kingdom . |
| 32 14 354 | 10/1983 | Germany . | | 2 087 240 | 9/1984 | United Kingdom . |
| 32 45 196 | 11/1986 | Germany . | | 2 087 731 | 9/1984 | United Kingdom . |
| 41 14 839 | 11/1992 | Germany . | | 2 087 730 | 12/1984 | United Kingdom . |
| 4720257 | 9/1972 | Japan ................................ 156/209 | | 2 171 915 | 9/1986 | United Kingdom . |
| 61 2854 | 1/1986 | Japan . | | 2 186 233 | 8/1987 | United Kingdom . |
| 1 122 727 | 8/1989 | Japan . | | 2 242 348 | 10/1991 | United Kingdom . |
| 89 01 653 | 1/1990 | Netherlands . | | 88/05269 | 7/1988 | WIPO . |
| 57626 | 11/1985 | Rep. of Korea . | | 89/10084 | 11/1989 | WIPO . |
| 1 132 120 | 10/1968 | United Kingdom . | | 89/10109 | 11/1989 | WIPO . |
| 1 259 983 | 1/1972 | United Kingdom . | | 90/14061 | 11/1990 | WIPO . |
| 1 432 978 | 4/1976 | United Kingdom . | | 91/02643 | 3/1991 | WIPO . |
| 1 509 229 | 5/1978 | United Kingdom . | | 91/10415 | 7/1991 | WIPO . |
| 1 519 172 | 7/1978 | United Kingdom . | | 91/14414 | 10/1991 | WIPO . |
| 1 535 607 | 12/1978 | United Kingdom . | | 93/10300 | 5/1993 | WIPO . |

5,667,625

APPARATUS FOR FORMING A FIBROUS LAMINATED MATERIAL

This application is a continuation of application Ser. No. 08/353,581 entitled "Fibrous Laminated Web And Method And Apparatus For Making The Same" and filed in the U.S. Patent and Trademark Office on Dec. 12, 1994, now abandoned, which is a continuation application of U.S. Ser. No. 07/973,146 entitled "Fibrous Laminated Web And Method And Apparatus for Making The Same" and filed in the U.S. Patent and Trademark Office on Nov. 6, 1992 now abandoned. The entirety of these Applications is hereby incorporated by reference.

BACKGROUND OF THE INVENTION

This invention generally relates to fibrous web laminates suitable for use in articles used to absorb, distribute and retain body liquids, such as disposable diapers, sanitary napkins, incontinence garments and the like, and to a method and apparatus for making same. More specifically, this invention relates to a nonwoven laminated material having improved liquid distribution and management and air circulation properties as well as enhanced comfort and softness when placed in contact with human skin.

Nonwoven materials, such as spunbonded webs and carded webs, have been used as bodyside liners in disposable absorbent articles. Typically, very open, porous liner structures have been employed to allow liquid to pass through them rapidly, thereby keeping the wearer's skin separate from the wetted absorbent core underneath the liner. Also, other layers of material, such as those constructed with thick, lofty fabric structures, have been interposed between the liner and absorbent pad for the purpose of reducing flowback.

U.S. Pat. No. 4,761,322 to Raley discloses a fibrous web laminate wherein a fibrous layer having a soft texture is laminated with a contiguous layer having a greater structural integrity such that the soft texture layer may be utilized as a skin-contacting surface and the contiguous layer thereto may provide mechanical strength and integrity to the laminate. The laminate of this patent includes a first fibrous layer, which is pattern bonded in a first spaced-apart bonding pattern, formed, for example, by passing the first layer through the nip formed by a first heated pattern roll and a smooth roll, and a second fibrous layer, which is pattern bonded in a second spaced-apart bonding pattern, formed, for example, by passing the first and second layers through the nip formed by a second heated pattern roll and a smooth roll. The second bonding pattern further produces bonds between the first and second layers, while the first bonding pattern does not.

U.S. Pat. No. 4,392,862 to Marsan et al. discloses an absorptive device including a facing element, a support element, an absorbent core and a backsheet. The facing element is a fluid permeable, unbonded, carded web of hydrophobic, thermoplastic fibers. The facing element is bonded in spaced apart bonding regions to a fluid permeable support element of nonwoven polyester or monofilament scrim.

U.S. Pat. No. 4,088,726 to Cumbers discloses a method of making nonwoven fabrics wherein a nonwoven web of thermally bondable material is passed through a nip between co-operating calender rolls, at least one of which is heated, with one calender roll having a surface pattern consisting of continuous lands and the other calender roll having a surface pattern consisting of lands that are isolated projections and the centroids of area of those projections concurrently in the nip being disposed at differing distances from the longitudinal axis of the nearest continuous land surface so that lands that oppose each other in the nip overlap to different extents.

Notwithstanding the development of nonwoven materials of the types described above, the need remains for a nonwoven material that can provide improved liquid intake and distribution as well as air circulation when used as a body contacting layer in a disposable absorbent article, resulting in greater surface dryness and comfort for the wearer's skin. There also is a need for a nonwoven material that exhibits improved softness and comfort when placed in contact with the wearer's skin.

SUMMARY OF THE INVENTION

This invention relates to a nonwoven laminated material wherein a first nonwoven layer comprising a plurality of staple fibers or continuous filaments of a thermoplastic material and a second nonwoven layer comprising a plurality of staple fibers or continuous filaments of two or more thermoplastic materials are bonded together in a spaced apart bonding pattern having apertures formed therein to form a nonwoven laminate having improved liquid distribution and management properties as well as enhanced comfort and softness when placed in contact with human skin. Also disclosed are a method and apparatus for making such a nonwoven laminate.

BRIEF DESCRIPTION OF THE DRAWINGS

The nonwoven laminated material of this invention will be better understood by reference to the following description of an embodiment of the invention taken in conjunction with the accompanying drawings.

FIGS. 3b and 3c are enlarged views of portions of the outer surfaces of the thermal bonding rolls of FIG. 3a;

DETAILED DESCRIPTION

The present invention comprehends a laminated fibrous fabric or material having a first fibrous layer comprising a plurality of staple fibers or continuous filaments of one or more thermoplastic materials and a second fibrous layer comprising a plurality of staple fibers or continuous filaments of two or more thermoplastic materials. The first layer and second layer, which can be nonwoven webs, are formed into a fibrous laminate by a spaced apart bonding pattern, such as by thermal bonding between a pair of heated embossing or bonding rolls having raised bonding patterns on the outer surfaces thereof. This spaced apart bonding pattern provides high structural integrity between the first and second layers without compromising the flexibility and soft surface texture of the first layer or the loftiness of the resulting fibrous laminate. Apertures are formed in the spaced apart bonding areas to enhance liquid distribution and air circulation through the respective layers of the fibrous laminate. The fibrous laminate formed in accordance with the present invention exhibits improved liquid intake and distribution and air circulation characteristics, resulting in greater surface dryness and comfort when placed against human skin. The fibrous laminate of this invention further provides a lofty, pillowed structure that exhibits improved softness and cushiony feel to the user. Other attributes and advantages of the present invention will be apparent from the ensuing disclosure and appended claims.

As used herein, the terms "nonwoven web" and "nonwoven layer" mean a fibrous web or layer having a structure of individual fibers or filaments that are interlaid in a random pattern. Nonwoven webs have been formed in the past, as known to those of ordinary skill in the art, by a variety of processes, such as, for example, meltblowing, spunbonding, air-laying, wet-laying, dry-laying, dry staple and carded web processes. While nonwoven webs can be used in practicing the present invention, the invention is not to be considered limited to nonwoven materials and other suitable fibrous structures may be employed.

The fibrous laminated material of this invention will be described herein in connection with its use in disposable absorbent articles, however, it should be understood that potential applications of this invention need not be limited to such disposable absorbent articles. As used herein, the term "disposable absorbent article" means an article that is used to absorb and retain body exudates and is intended to be discarded after a limited period of use. Such articles can be placed against or in close proximity to the body of the wearer to absorb and retain various exudates discharged from the body.

Figure 1:
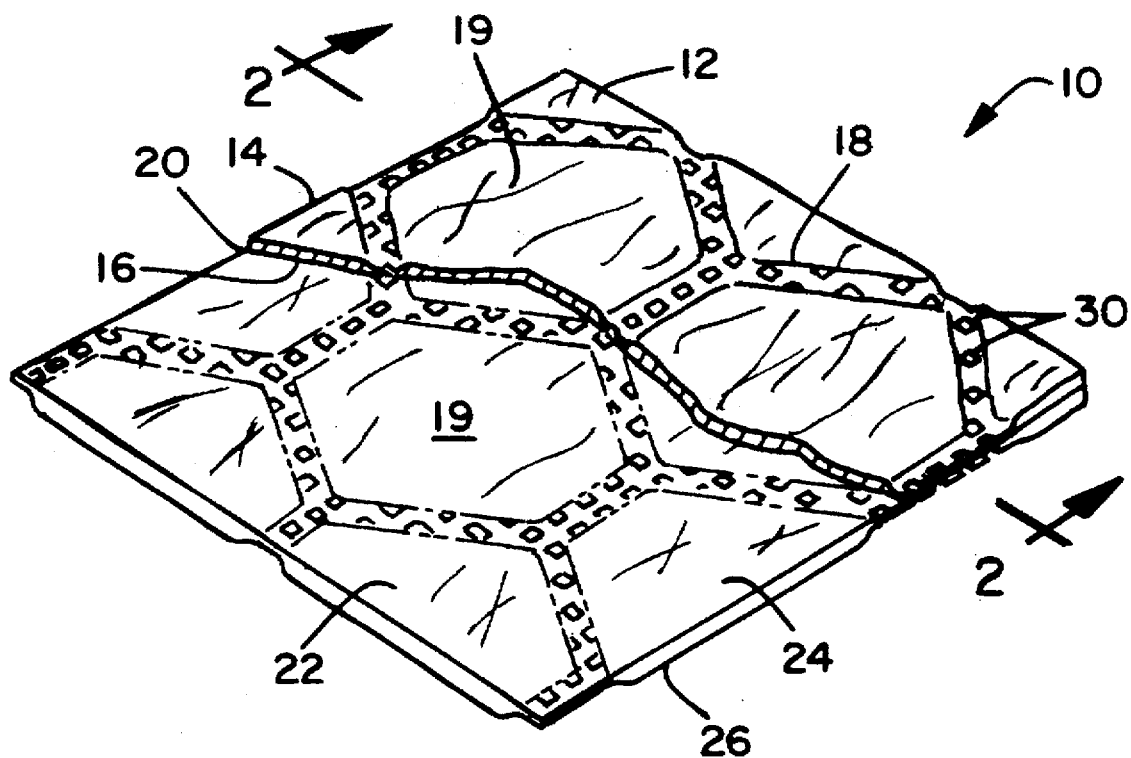
FIG. 1 is a perspective partial sectional view of a nonwoven laminated material according to the present invention.

Referring now to FIG. 1, a perspective partial sectional view of an embodiment of the present invention is shown. The nonwoven material 10 comprises a first nonwoven layer 12 and a second nonwoven layer 22. The first layer 12 has an upper surface 14 and a lower surface 16 and the second layer 22 has an upper surface 24 and a lower surface 26. In the embodiment shown, a plurality of thermal fusion bonds in a spaced apart bonding pattern 18 extend through the thickness of the nonwoven material 10 to thermally fuse or bond fibers of first layer 12 with fibers of second layer 22 at the interface 20 therebetween. Bonding of the first and second layers is substantially limited to the bonding regions 18. That is, in the areas 19 of the first and second layers outside of the bonding pattern 18, the fibers of the respective layers are only lightly bonded to one another by fiber fusing from thermal energy. Thus, the bonding regions 18 are separated or "spaced apart" by lightly bonded areas 19. Also as shown in this embodiment, apertures 30 are formed within the bonding areas 18 to improve the liquid distribution rate and air circulation of the nonwoven material 10.

The respective first and second fibrous layers of the present invention may be formed by any suitable natural or synthetic fibers in any appropriate structure, although in the embodiments shown in the accompanying drawings, these fibers are formed into nonwoven layers. In general, each nonwoven layer of the present invention can be prepared from noncontinuous fibers, continuous filaments or a combination thereof. The method of producing each layer in the embodiment shown employs dry staple processes, or more specifically, carded web techniques, as known to those of ordinary skill in the art. While carded web techniques can be advantageously employed in forming the respective layers of the present invention, spunbonding, meltblowing, air-laying and other techniques known to those of ordinary skill in the art that produce noncontinuous fibers and continuous filaments are also considered within the scope of this invention. Carded webs suitable for use in the practice of the present invention can have the fibers in an aligned or an unaligned configuration. Conventional carding machines, as known to those of ordinary skill in the art, can be employed in producing the respective layers of the present invention.

Commercially available thermoplastic polymeric materials can be advantageously employed in both layers of the present invention. Examples of such polymers, by way of illustration only, include polyolefins, polyamides, polyesters and the like. The fibers may have any suitable morphology and may include hollow or core fibers, shaped fibers, bicomponent fibers or high absorbent particle impregnated fibers.

In the embodiment shown in FIG. 1, the first nonwoven layer 12 of the nonwoven fabric 10 is a bonded carded web made of thermoplastic polypropylene fibers. The second nonwoven layer 22 of the nonwoven fabric is a substantially unbonded or unbonded carded web made of a blend of polypropylene and polyester fibers. By "substantially unbonded" as used herein is meant a web with fibers that are sufficiently bonded together, by known bonding processes, for handling the web, but insufficiently bonded to provide the needed strength and integrity for the end-use application. By "unbonded" as used herein is meant a web with fibers that are not mechanically, thermally nor chemically bonded together.

The ratio of different thermoplastic fibers in the second layer 22 can be varied as appropriate for the intended end-use application of the nonwoven material. For example, the ratio of polypropylene to polyester fibers by total weight of the second layer 22 can range from about 70:30 to about 25:75, with about 40:60 being the ratio for the embodiment shown.

It is an important advantage of the present invention that certain materials that might not have optimum properties in a nonwoven web for various reasons may be used in the present invention in combination with a web made from one or more different materials to produce a better set of properties. For example, an unbonded or substantially unbonded nonwoven layer of polypropylene and polyester fibers may be considered too soft and weak for certain nonwoven web applications. However, in following the teachings of the present invention, a nonwoven layer made of an appropriate blend of polypropylene and polyester fibers can be bonded to a stronger nonwoven web, such as a bonded layer of polypropylene fibers, to thereby make a more desirable nonwoven laminate.

The fiber sizes, basis weights and densities of the fibrous layers comprising the nonwoven fabric 10 of the present invention also can be readily varied depending on the intended use of the web. For example, in one application of the present invention, the nonwoven material can be used as a body facing layer for a disposable absorbent article having an absorbent core placed between the liner and an outer cover. Such disposable articles include, by way of illustration only, diapers, training pants, sanitary napkins, incontinence garments and the like. For this application, the polypropylene fibers of the first layer 12 can be as fine as about 1.0 denier (12.5 µm in diameter) to as coarse as about 3.0 denier (21.6 µm) and have a crimped fiber length of from about 1.25 in. (31.75 mm) to about 2.5 in. (63.5 mm), although it is desireable for the user's comfort that the fibers be from about 2 denier (17.6 µm) to about 2.2 denier (18.5 µm) and have a crimped fiber length of about 1.5 in (38.1 mm). (It is known in the art that crimping is a function of fiber type, diameter and density.) The finer fiber size of the polypropylene fibers in the first layer 12, which in this application comes into contact with human skin and functions as a liner layer, yields a softer surface texture for the first layer 12. The polypropylene fibers in the second layer 22 can, but need not, be identical to the polypropylene fibers in the first layer 12. The polyester fibers in the second layer can be from about 3 denier (17.5 µm) to about 9 denier (30.4 µm) and have a crimped fiber length of from about 1.25 in. (31.75 mm) to about 3 in. (76.2 mm), with polyester fibers of 6 denier (24.8 µm) having a crimped fiber length of about 2 in. (50.8 mm) being suitable. While not wishing to be bound by any particular theory, it is currently believed that the use of different fibers enhances the liquid wicking and distribution properties of the second layer 22. The fibers in the first layer 12, which have the same diameters, tend to form similarly sized pores in a single plane, while the fibers in the second layer 22, which have different diameters, tend to form pores of varying sizes in multiple planes. The differing pore sizes in multiple planes in second layer 22 are believed to enhance wicking of liquid throughout the second layer 22 and liquid intake into and distribution through the second layer 22. It is further currently believed that the resiliency of the polyester fibers is a contributing factor to the improved liquid management and air circulation characteristics of the nonwoven laminate of this invention. Consequently, in this application, the second layer 22 functions as a surge layer or temporary reservoir for the liquid passing through the nonwoven material 10 into the absorbent core of an absorbent article.

The nonwoven material 10 of this invention can have a basis weight from about 25 g/m$^2$ (0.7 oz/yd$^2$) to about 78 g/m$^2$ (2.3 oz./yd$^2$), a thickness of from about 0.03 in. (0.76 mm) to about 0.08 in. (2.03 mm) and a density of from about 0.020 g/cc to about 0.050 g/cc. Density is determined using the following equation:

$$\frac{\text{Basis Weight (g/m}^2\text{)} \times 0.0000394}{\text{Thickness (in.)}} = \text{Density (g/cc)}$$

For example, in the embodiment shown, the basis weight for the nonwoven web 10 can range from about 47 g/m$^2$ (1.4 oz/yd$^2$) to about 58 g/m$^2$ (1.7 oz/yd$^2$), the thickness can range from about 0.04 in. (1.02 mm) to about 0.06 in. (1.52 mm) and the density can range from about 0.030 g/cc to about 0.045 g/cc.

The basis weight of the nonwoven material 10 was measured using a device that measures the weight of a sample of the nonwoven material. Each sample measured no less than 4 in$^2$ (2580 mm$^2$). Each sample was cut, smoothed to eliminate folds or wrinkles, and weighed on an analytical balance to the nearest 0.01 g. The basis weight then was calculated by dividing the sample weight by the sample area.

The thickness of the nonwoven material 10 was measured using a device that applies a constant loading pressure of 0.05 psi (35.15 kg/m$^2$) to a sample of the nonwoven material. Each sample measured at least 5×5 in. (127×127 mm). Each sample was cut out, smoothed to eliminate folds or wrinkles, placed under a circular plexiglass platen (foot) having a 3 in. (76.2 mm.) diameter, centered as much as possible, and the platen then was lowered onto the specimen. The thickness of each sample was recorded to the nearest 0.001 in. (0.0254 mm).

Although in alternative embodiments, the basis weight and density of the first layer 12 prior to bonding to the second layer 22 can vary in relation to that of the second layer 22, the embodiment shown includes a first layer 12 having a lower basis weight and a higher density than the second layer 22. The basis weight for the first layer can range from about 0.4 oz/yd$^2$ (16 g/m$^2$) to about 0.8 oz/yd$^2$ (28 g/m$^2$), with about 0.5 oz/yd$^2$ (18 g/m$^2$) to about 0.6 oz/yd$^2$ (22 g/m$^2$) being desireable, and the basis weight for the second layer can range from about 0.7 oz/yd$^2$ (24 g/m$^2$) to about 1.02 oz/yd$^2$ (35 g/m$^2$), with about 0.9 oz/yd$^2$ (32 g/m$^2$) being desireable. The density for the first layer can range from about 0.050 g/cc to about 0.065 g/cc, with about 0.055 g/cc being desireable, and the density for the second layer can range from about 0.024 g/cc to about 0.045 g/cc, with about 0.035 g/cc being desireable.

Figure 2:
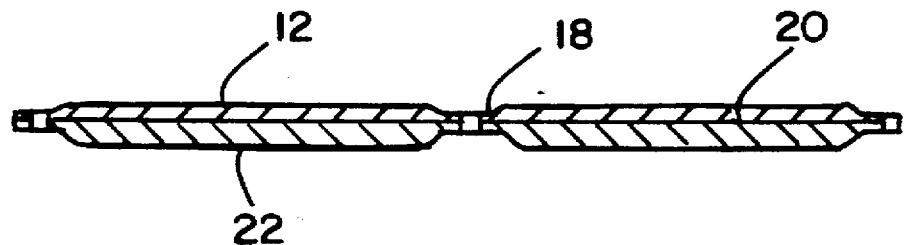
FIG. 2 is a cross-sectional elevational view of the nonwoven laminated material of FIG. 1 taken along line A—A of FIG. 1.

Referring now to FIG. 2, a cross-sectional view of the embodiment of the nonwoven material 10 of the present invention described above is shown, comprising a first nonwoven layer 12 and a second nonwoven layer 22. A series of bonds forming a spaced apart bonding pattern 18 extend through the thicknesses of the respective layers and bond the first layer 12 to the second layer 22 at the interface 20 in the bonding regions 18. The manner of forming the spaced apart bonding pattern 18 now will be described.

The spaced apart bonding regions 18 may be produced by any suitable method of bonding the respective first and second layers to one another at the interface 20 therebetween that yields a nonwoven material 10 having the liquid management, air circulation and other properties described herein. Thermal bonding, which includes the use of a pair of heated embossing rolls, is considered a useful method of forming the bonding pattern 18, as described in greater detail hereinbelow.

The present invention contemplates bonding of the respective layers in various sequences. For example, the first layer 12 may be formed and bonded in a first operation, with the second layer 22 formed in a second operation and then bonded to the first layer 12 in yet a further operation. Alternatively, the first layer 12 may be formed in a first operation, the second layer 22 formed in a second operation, and the respective layers bonded together in still another separate operation which simultaneously bonds the fibers in the first layer 12 to one another. The thermoplastic fibers of second layer 22, which are initially unbonded or substantially unbonded, do have a degree of thermal bonding when formed into the nonwoven laminated material 10, as further described below.

In the embodiment shown, the fibers of the first layer 12 have a greater extent of bonding relative to the fibers of the second layer 22. For example, first layer 12 may be thermobonded by passing the layer 12 between a pair of bonding rolls of conventional construction (i.e., an engraving roll and a smooth roll) heated to a temperature of between 270° F. (132° C.) and 300° F. (149° C.), with 275° F. (135° C.) to 285° F. (141° C.) being desireable. The appropriate temperature for bonding layer 12 using thermal bonding rolls will vary depending upon the rotational surface speeds and diameters of the bonding rolls and the thermoplastic fibers used. The first layer 12 may alternatively be bonded by other known bonding processes, such as by pattern adhesive bonding, needling or hydro or airjet entangling of the fibers. In this embodiment, the first layer 12 has a higher density than the second layer 22. In this way, the first layer 12, which has greater structural integrity and mechanical strength than the second layer 22, can provide a base substrate for the second layer 22.

The degree of bonding of the first layer 12 to the second layer 22 may be controlled in the spaced apart bonding region 18 by altering the percent bond area, which refers to the surface area of the interface between the respective layers that is occupied by bonds within the bonding regions. Thus, as shown in FIGS. 1 and 2, the interface 20 of the first layer 12 and second layer 22 has a spaced apart pattern of bonds 18 disposed across its surface and the ratio of the surface area occupied by the bonding regions 18 to the total area of the surface of the interface 20 is the percent bond area for the interface 20. In the embodiment shown, the percent bond area of the nonwoven laminate can range from about 1% to about 6%, with about 2% to about 4% being desireable. While a hexagonal (honeycomb-like) bonding pattern is shown in this embodiment, the present invention encompasses other geometric, non-geometric, repeating and non-repeating bonding patterns, which are suitable for incorporation into the nonwoven material of the present invention.

Figure 3:
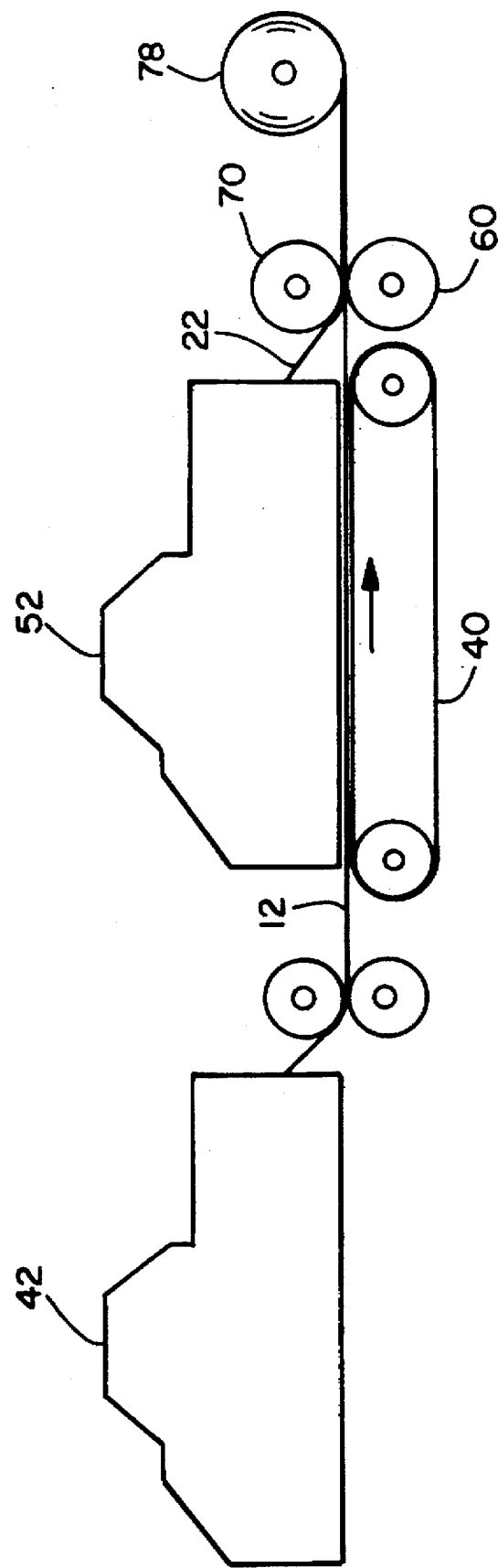
FIG. 3 is a schematic diagram showing process apparatus for forming a nonwoven laminated material in accordance with the present invention.

FIG. 3 is a schematic diagram of the apparatus used for forming the above-described embodiment of the nonwoven laminated material of the present invention. As stated above, conventional carding machines, such as described in U.S. Pat. Nos. 3,604,062 and 3,604,475, can be employed in producing the respective layers of the present invention. As shown, the first carding machine 42 lays down the first layer 12 on a moving belt 40, while the second carding machine 52 lays down the second layer 22 on top of the first layer 12. In this way, first layer 12 acts as a base substrate for second layer 22 as the two layers pass through the forming process.

Optionally, the two layers may be passed through a pair of compacting rollers that slightly compact the fibrous webs to thereby increase the integrity of the webs and to aid in further processing. One or both of the layers also may be passed through apparatus that orients the fibers in the web to optimize material strength in the machine direction (MD) and cross direction (CD). As used herein, machine direction (MD) refers to the direction in which the web was laid down (from left to right in FIG. 3) and cross direction (CD) refers to the axis perpendicular to the direction in which the web was laid down. MD strength for the nonwoven laminate of this invention must be sufficiently high (at least about 900 g/in. (354 g/cm) to about 2700 g/in. (1062 g/cm), with at least about 1300 g/in. (512 g/cm) being desireable) so that the nonwoven webs will not be broken during high speed manufacturing processes used for producing disposable absorbent articles, such as diapers.

The two nonwoven layers next pass through the two bonding rolls 60 and 70. In the embodiment shown in FIGS. 3 and 3a, both bonding rolls are heated and have raised (male) bonding patterns on the outer surfaces thereof. The lower roll 60 has a spaced apart bonding pattern 62 on its surface, while the upper roll 70 has raised bonding points 72 on its surface. In alternative embodiments, the positions of the bonding rolls can be reversed. It is a feature of this invention, therefore, that thermal bonding rolls having different male or raised bonding patterns on each of the outer surfaces thereof are employed to create a spaced apart bonding pattern for bonding together the respective layers of the nonwoven material.

As the two nonwoven layers 12 and 22 pass between these two heated rolls 60 and 70, each layer becomes stabilized by the formation of discrete compacted bonding areas 18 of thermally induced fiber bonds that extend through a major portion of the thickness of each nonwoven layer. The thickness of the compacted or bonded regions 18, which may vary depending upon the thicknesses of the respective layers 12 and 22, can range from about 50 µm to about 150 µm, with about 70 µm to about 110 µm being used in the embodiment shown herein. The compacted bonded areas of nonwoven material 10 are distributed in a bonding pattern 18 formed by the points of contact between the raised bonding patterns on the two heated rolls 60 and 70, with lightly bonded fiber spans 19 therebetween.

Figure 5:
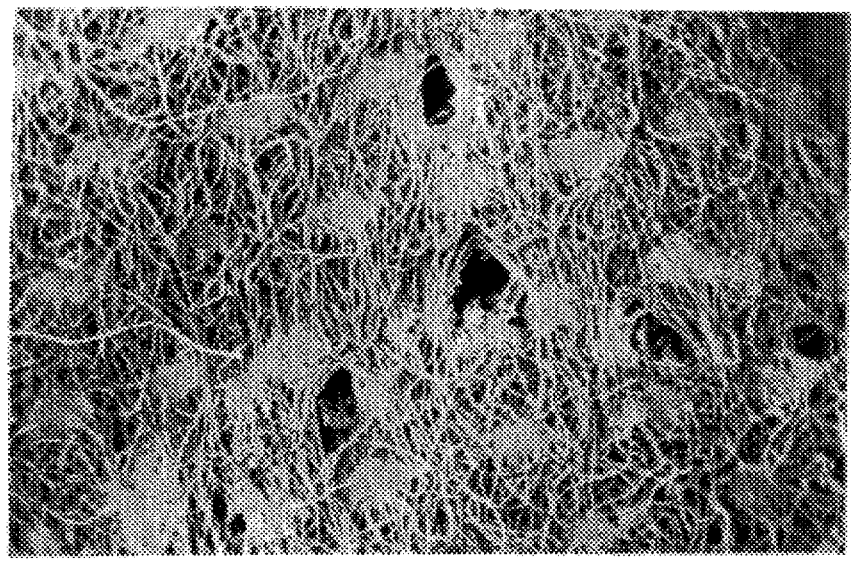
FIG. 5 is a photomicrograph (13.2 magnification, 12 mm working distance, 5 KV accelerating voltage) of a portion of the apertured bonding region of the nonwoven laminated material of the present invention, with the first layer of the nonwoven laminated material facing the viewer.
Figure 6:
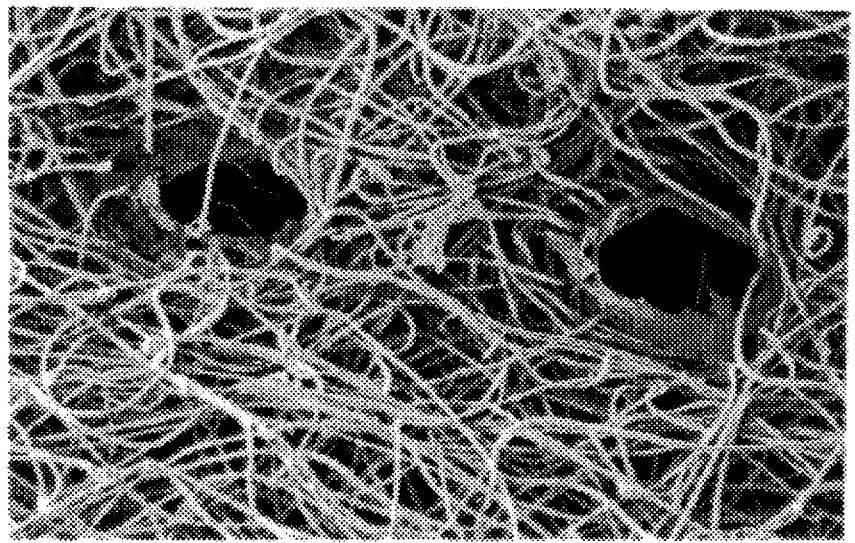
FIG. 6 is a photomicrograph (28.7 magnification, 12 mm working distance, 5 KV accelerating voltage) of a portion of the apertured bonding region of the nonwoven laminated material of the present invention, with the second layer of the nonwoven laminated material facing the viewer.

Apertures 30 are formed in the bonded areas 18 formed by the points of contact between the raised patterns on the heated bonding rolls 60 and 70, as described in greater detail below. While the exact size and shape of the apertures 30 are not considered critical by the inventor (see FIGS. 5 and 6), apertures having average diameters ranging from about 8 µm to about 580 µm or more can be advantageously employed in the present invention, with aperture average diameters from about 29 µm to about 277 µm being desireable. As shown in FIGS. 5 and 6, the apertures 30 are substantially free of fibers throughout the thickness of the nonwoven laminated material 10 and provide a non-tortuous pathway for liquid to pass through the nonwoven material 10. The apertures 30, consequently, allow rapid liquid intake through the first layer 12 into the second layer 22 and finally into the absorbent core of an absorbent article. It has been observed that liquid primarily flows away from the point of contact with the nonwoven material 10 along the apertured bonding regions 18, which act as channels for the liquid. The apertures 30 are to be distinguished from the pores formed between fibers in layers 12 and 22, which are not sufficiently large nor non-tortuous to allow such rapid liquid intake and distribution. Consequently, a nonwoven fabric 10 is shown having spaced apart bonded areas 18 with lightly bonded areas 19 therebetween and apertures 30 formed in the bonded areas 18.

Two parameters of concern in regard to the specific combination of raised patterns on the bonding rolls that are used are the size of the raised bonding areas of the bonding rolls and the distance or spacing separating the bonding areas. These two parameters together affect the percentage of area on the nonwoven material 10 that becomes bonded, as described above. It is important that the percent bond area be great enough to insure sufficient integrity of the web for its intended use. On the other hand, it is important that the percent bond area not be too great, as a higher percent bond area usually produces a web with reduced softness. The percent bond area of the lower roll 60 (the ratio of the surface area of the raised bonding pattern 62 to the total area of the outer surface of lower roll 60) of this embodiment can range from about 9% to about 20%, with about 18% to about 19.5% being desireable. The percent bond area of the upper roll 70 (the ratio of the surface area of the raised bonding points 72 to the total area of the outer surface of lower roll 70) of this embodiment can range from about 10% to about 30%, with about 11% to about 20% being desireable. As noted above, the percent bond area of the nonwoven laminate 10, which is the mathematical product of the percent bond areas of the upper roll 70 and lower roll 60, can range from about 1% to about 6%, with about 2% to about 4% being desireable.

It is further important that the raised bonding patterns of the two bonding rolls be combined to optimize the number of apertures within the bonded areas. In the embodiment shown in FIGS. 3a, 3b and 3c, the width of the raised bonding pattern 62 on the outer surface 64 of the lower roll 60 can range from about 0.04 in. (1.0 mm.) to about 0.08 in. (2.0 mm.), with a width of about 0.07 in. (1.8 mm.) being desireable, and the width at the base 66 of the raised bonding pattern 62 can range from about 0.06 in. (1.6 mm) to about 0.12 in. (3.1 mm), with about 0.11 in. (2.8 mm) being desireable. The raised bonding pattern 62 of the lower roll 60 in this embodiment has an engraving depth of about 0.04 in. (1.0 mm), which is the distance between the outer surface 64 and base 66 of the raised bonding pattern 62. The individual hexagons 68 of the raised bonding pattern 62 of lower roll 60 can have a repeating width W of from about 0.65 in. (16.50 mm) to about 0.68 in. (17.33 mm), a repeating height H of from about 1.10 in. (28 mm) to about 1.18 in. (30 mm), and a pitch P of about 0.65 in. (16.50 mm) to about 0.68 in. (17.33 mm) at a pitch angle of from about 45° to about 60°.

Figure 3A:
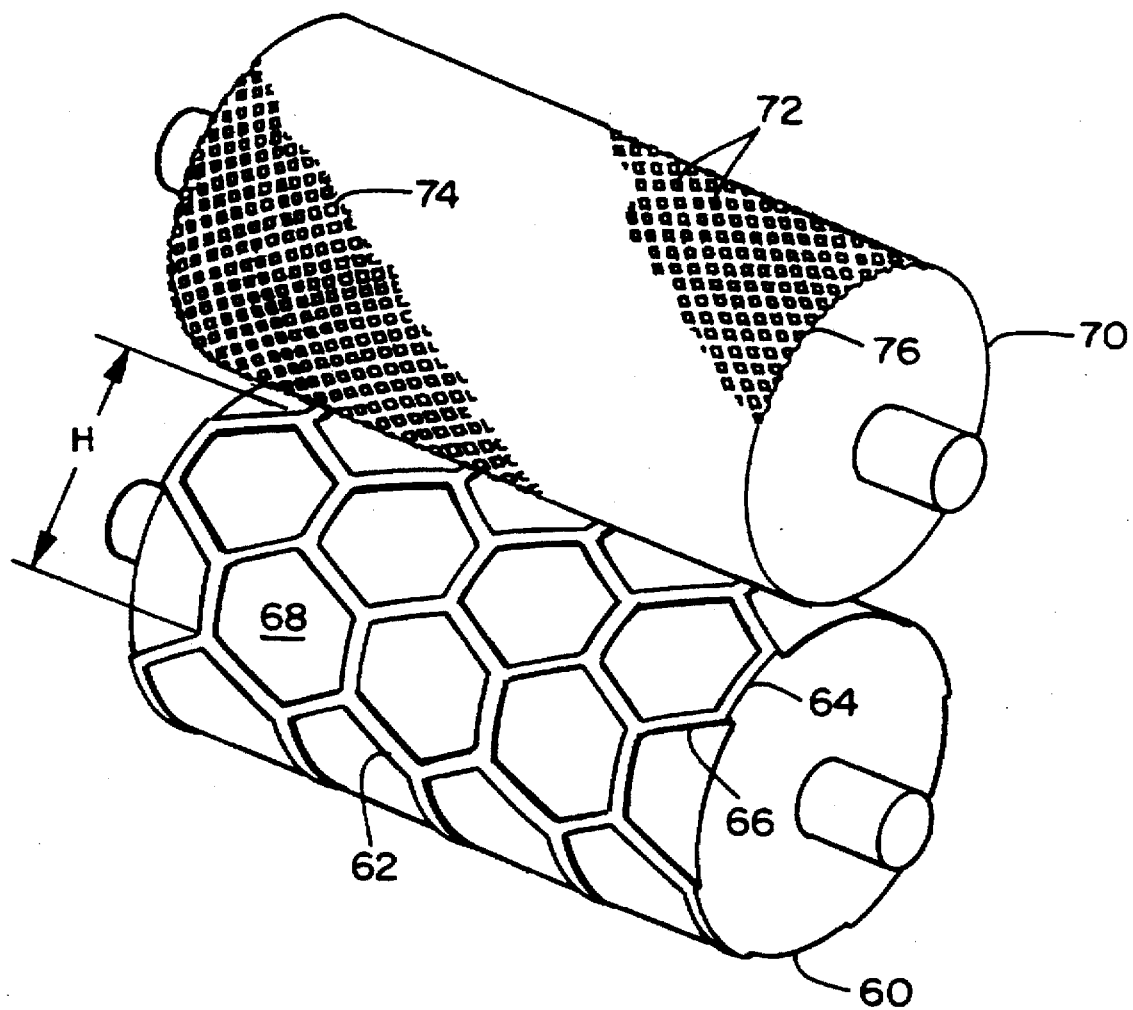
FIG. 3a is a perspective view of thermal bonding rolls for forming a nonwoven laminated material in accordance with the present invention.
Figure 3B:
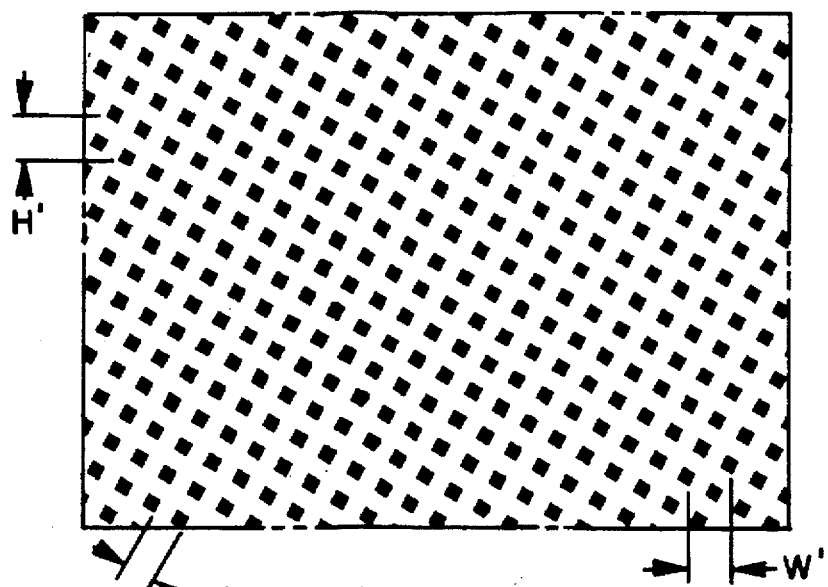
Figure 3C:
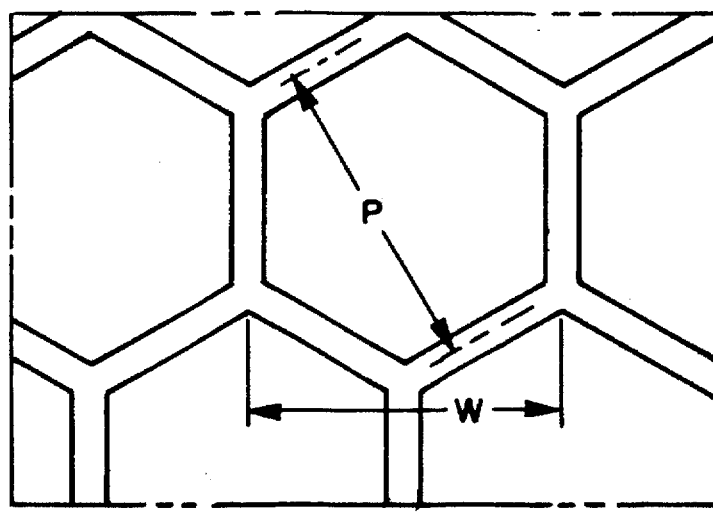

Still referring to FIGS. 3a, 3b and 3c, the width of the raised bonding points 72 on the outer surface 74 of the upper roll 70 can range from about 0.028 in. (0.70 mm) to about 0.031 in. (0.80 mm), with a width of about 0.030 (0.75 mm) being suitable. As is conventional in the art, the width at the base 76 of the raised bonding points 72 is slightly greater than the width on the outer surface 74. The raised bonding points 72 of the upper roll 70 can have an engraving depth of about 0.026 in. (0.65 mm). The individual raised bonding points 72 in this embodiment are arranged at about 218.0 bonding points/in$^2$ (33.8 bonding points/cm$^2$) and have a repeating width W' of about 0.094 in. (2.4 mm) to about 0.118 in. (3.0 mm), a repeating height H' of about 0.068 in. (1.72 mm), and a pitch P' of about 0.068 in. (1.72 mm) at a pitch angle of from about 30° to about 45°. While in the embodiment shown, the outer surface 74 of the raised bonding points 72 is in the form of a square, other geometric and non-geometric shapes may be employed as the raised bonding points 72 of upper roll 70.

The inventor has observed in optimizing the nonwoven material 10 of the present invention, the following factors are interrelated:
1) Temperature of bonding rolls 60 and 70;
2) Line speed of the forming process;
3) Nip pressure between the bonding rolls;
4) Diameter of the bonding rolls; and
5) Types of materials used in forming layers 12 and 22.

That is, modifying one or more of the above factors tends to affect the remaining factors as well. For example, an increase in the line speed of the forming process results in the layers of the nonwoven laminate being in contact with the bonding rolls for a shorter period of time. Consequently, the temperature of the bonding rolls may have to be increased to achieve the required degree of bonding of the two layers, thereby compensating for the change in line speed.

As noted above, an important factor relating to the bonding of the two layers is the temperature at which the bonding rolls 60 and 70 are maintained. Naturally, temperatures below a certain point for each polymer will not effect any bonding, while temperatures above another point will melt too much of the web. Also, its has been observed that the temperature of the bonding rolls can affect both the tensile strength and softness of the nonwoven laminate produced. In particular, within a certain range, higher temperatures will produce a web with higher tensile strength. However, these same higher temperatures can produce a web with decreased softness. This is likely due to a higher and lower degree of bonding that occurs within this range of temperatures. That is, the higher temperatures likely result in more and stronger interfilament bonding that is beneficial to tensile strength and somewhat detrimental to softness. In addition, higher temperatures likely result in a less lofty, pillowed structure, as the thermoplastic fibers experience more shrinkage, adversely affecting the softness and cushiony feel of the nonwoven material 10.

It has further been observed that the temperature of the rolls can affect the formation of apertures in the bonded areas of the web. While the apertures formed in the bonded areas are not solely thermally produced, thermal bonding allows the respective layers to be compressed to a sufficient degree that mechanical aperturing may occur, as further described below.

In the embodiment shown, the bonding temperature for lower roll 60 can range from about 260° F. (127° C.) to about 285° F. (141° C.), with a temperature of about 265° F. (129° C.) to about 275° F. (135° C.) being desireable, and the bonding temperature for upper roll 70 can range from about 270° F. (132° C.) to about 320° F. (160° C.), with a temperature of about 290° F. (143° C.) to about 315° F. (157° C.) being desireable. It is important that the bonding roll that contacts the first nonwoven layer 12, which in this embodiment is lower bonding roll 60, have a lower temperature than the bonding roll that contacts the second nonwoven layer 22, which in this embodiment is upper roll 70, such that the softness of the first layer 12 is not significantly reduced, while the thermoplastic fibers in the second layer 22 are sufficiently heated to thermally fuse with the thermoplastic fibers in the first layer 12. So long as the temperature of bonding roll 60 is maintained at a slightly lower temperature than the temperature at which the first layer 12 is bonded, assuming all other operating parameters are constant for the forming process described above, the softness of layer 12 will not change significantly.

Another important factor relating to the bonding of the two layers as well as the formation of apertures in the bonding regions is the line speed at which the respective bonding rolls are operated. In the embodiments shown, the rolls can operate at line speeds ranging from about 65 feet/in. (20 m/min.) to about 328 feet/min. (100 m/min.) or more. It has further been observed that aperture formation within the bonding regions can be significantly improved by employing different rotational surface speeds for the two bonding rolls. The difference in rotational surface speeds can differ from about 4% to about 20%, with about 5% to about 15% being conveniently employed. Either bonding roll may be employed with a higher rotational speed than the other bonding roll. While not wishing to be bound by any particular theory, it is believed that aperture formation is improved by operating the bonding rolls at different rotational speeds because the shearing forces tangential to the bonding roll surfaces in the thermally produced compacted bonding areas tear (mechanical aperturing) the nonwoven materials at the points of contact between the raised bonding patterns of the bonding rolls.

Another important factor relating to the bonding of the two layers is the diameter of each bonding roll. While in the embodiment shown (and in the ensuing Examples), the bonding rolls each are about 12 inches (305 mm) in diameter, bonding rolls having smaller or larger diameters are suitable for producing the nonwoven laminate of the present invention. Moreover, the diameters of the bonding rolls need not be identical.

Another important factor relating to the bonding of the two layers and aperture formation within the bonding regions is the nip pressure between the bonding rolls. In the embodiment shown, the bonding rolls produce a nip pressure of from about 60 pli (10 kg/lcm) to about 400 pli (67 kg/lcm). It is likely that higher nip pressures will result in a less lofty, pillowed structure, adversely affecting the softness characteristics of the nonwoven material 10.

In the embodiment shown, after the layers 12 and 22 of nonwoven laminated material 10 are bonded by bonding rolls 60 and 70, nonwoven material 10 is wound on a take up roll (winder) 78. Alternatively, it may be desirable to design this apparatus to connect with a fabrication line for the end product. Higher tension on the take up roll 78 or fabrication line is another factor that is likely to adversely affect the loftiness of the nonwoven material 10 of this invention.

Figure 4:
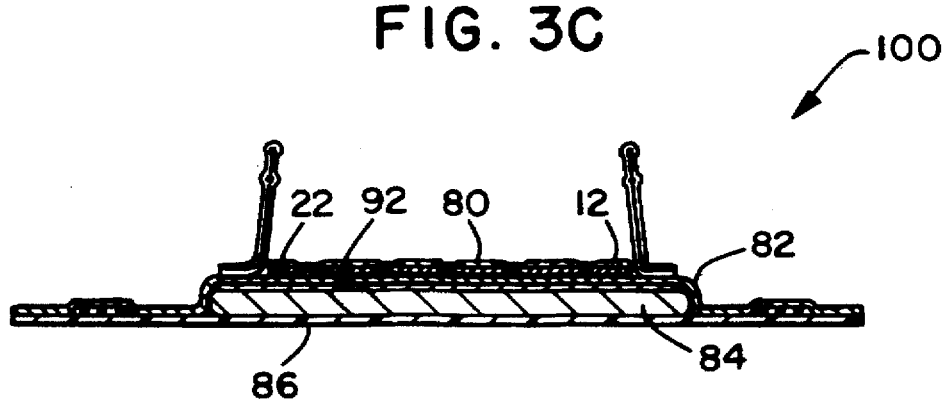
FIG. 4 is a cross-sectional view through a disposable diaper including the nonwoven laminated material of the present invention positioned on the side of the diaper that will be placed next to the infant's body.

FIG. 4 is a cross-sectional view through a disposable diaper 100 including the nonwoven material 80 of the present invention positioned on the side of the diaper that will be placed next to the infant's body. In the embodiment shown, the nonwoven material 80 forms a body facing outer layer 12 comprising a bonded carded web formed of polypropylene fibers and an inner "surge" layer 22 comprising a substantially unbonded or unbonded carded web formed of a blend of polypropylene and polyester fibers as described above. The diaper further includes a liquid-permeable bodyside liner 82 formed, for example, of nonwoven spunbond or bonded carded web material, an absorbent core 84 formed, for example, of a blend of hydrophilic cellulosic woodpulp fluff and highly absorbent gelling particles (e.g., superabsorbents), a tissue layer 92 surrounding at least a portion of absorbent core 84, and a flexible, liquid-impermeable outer cover 86 formed, for example, of thin polyethylene film. As used herein, the term "superabsorbent" refers to a material, natural or synthetic, capable of absorbing or gelling at least about 10 times its weight in liquid.

In the embodiment shown, the nonwoven material 80, which overlies liner 82, is substantially coextensive with the width of absorbent core 84, while the total area of liner 82 is substantially coextensive with the total area of outer cover 86. Alternatively, the nonwoven material 80 may be arranged to be generally coextensive with the outer cover 86. In other configurations, nonwoven material 80 may have a width that is less than the minimum width of absorbent core 84. In various optional configurations, the length of nonwoven material 80 may be equal to or less than the length of outer cover 86, although in the illustrated embodiment, the lengths of nonwoven material 80 and outer cover 86 are substantially equal.

As further shown in FIG. 4, nonwoven material 80 is positioned between two optional containment flaps 88 attached to the bodyside surface of liner 82. Suitable constructions and arrangements for containment flaps are described, for example, in U.S. Pat. No. 4,704,116, issued Nov. 3, 1987, to K. Enloe, the disclosure of which is hereby incorporated by reference.

Elastic members 90, which may optionally be included in the absorbent article, are disposed adjacent each longitudinal edge of diaper 100. Elastic members 90 are arranged to draw and hold the lateral, side margins of diaper 100 against the legs of the wearer. Additionally, elastic members (not shown) also may be disposed adjacent either or both of the end edges of diaper 100 to provide an elasticized waistband.

Nonwoven material 80 is connected to or otherwise associated with bodyside liner 82 or outer cover 86 in an operable manner. As used herein, the term "associated" encompasses configurations where nonwoven material 80 is directly joined to bodyside liner 82 by affixing marginal areas or intermediate areas of nonwoven material 80 directly to liner 82, and configurations where nonwoven material 80 is joined to outer cover 86, either directly or by affixing nonwoven material 80 to intermediate components that in turn are affixed to outer cover 86. Nonwoven material 80 may be affixed directly to bodyside liner 82 or outer cover 86 by attachment means (not shown) such as adhesive, sonic bonds, thermal bonds or any other attachment means known to those of ordinary skill in the art. It is readily apparent that such attachment means may also be used to interconnect and assemble together the other component parts of the diaper 100. Fastening means (not shown) of known construction may also be optionally incorporated in the diaper construction shown.

While a particular configuration of the component parts of diaper 100 is shown in FIG. 4, these components may be assembled into a variety of well-known diaper configurations. It should be further recognized, however, that in disposable absorbent articles other than diapers, individual components may be optional, depending upon their intended end uses.

An important property of any bodyside liner material is its softness. In particular, it is important for the liner to be both extremely pliable as well as soft to the touch in consideration of the infant's comfort. The present inventor has observed that the body facing layer 12 of the nonwoven material 80 of the present invention exhibits excellent softness characteristics.

Another important property of a nonwoven liner and nonwoven fabrics in general is tensile strength, i.e., the resistance to tearing, and percent elongation prior to tearing. These properties have been measured by the present inventor on a device, such as the Instron Model TM 1000 (Instron Corp. having offices in Canton Mass.), that grips a sample (about 1×6 in. (25.4×1524 mm)) of a nonwoven fabric in a pair of jaws extending the entire width of the sample, and then pulls it apart at a constant rate of extension. The force needed to rupture the fabric is recorded as the tensile strength and the length of the fabric before rupture as compared to the original length provides the percent elongation value. These tests can be performed either with the fabric oriented in the jaws so that the force is applied in the machine direction, MD, or with the fabric oriented so that the force is applied in the cross direction, CD. It was observed that the nonwoven materials made in accordance with the present invention, several examples of which are discussed below, exhibited sufficient tensile strength and percent elongation properties.

Yet another property that is particularly important for a liner of an absorbent article, such as a disposable diaper, is the wettability of the liner. Depending upon the design of the absorbent article, it is usually desirable to have the liner be at least partially wettable in order to facilitate passage of liquid through to the absorbent core. In addition, it is even more desirable to provide a wettability gradient in the liner whereby liquid can be wicked away from the wearer for increased comfort and skin health. In particular, it is desireable to provide, as in the present invention, a body facing layer 12 that is less wettable than the "surge" layer 22, i.e., the layer closest to the absorbent material. In this way, liquid flows more easily through to the absorbent core material than it flows back to the wearer.

Many of the polymers that are suitable to make nonwoven webs are hydrophobic. Specifically, polyolefin fibers are completely hydrophobic. As a result, it is desirable for nonwoven webs made with these polymers to impart a desired level of wettability and hydrophilicity. It is known in the art that wettability of hydrophobic fibers, such as polypropylene, can be increased by the application of water-soluble finishes, typically ranging from about 0.3% to about 0.6%, to the surfaces of such hydrophobic fibers for improving the liquid management properties of such fibers in their end-use applications. In the embodiment described herein, the polypropylene fibers employed can be made wettable by treating the fibers with water-soluble finishes before being formed into nonwoven layers 12 and 22.

Another contributing factor in producing the described wettability gradient is the blending of polyester fibers in a desired amount with the polypropylene fibers forming the second nonwoven layer 22. As described above, the differing pore sizes resulting from using the coarser, more resilient polyester fibers in a homogeneous blend of polypropylene and polyester fibers in nonwoven layer 22, produce the required wettability gradient between first layer 12 and second layer 22.

The following examples are provided to give a more detailed understanding of the invention. The particular compositions, proportions, materials and parameters are exemplary and are not intended to specifically limit the scope of the present invention.

EXAMPLES

Example 1

A first layer was formed of 100% polypropylene (PP-196 manufactured by Hercules, Inc. having offices in Wilmington, Del.) by blending on a conventional carding machine as described above. The first layer had a basis weight of about 18 g/m$^2$ (0.5 oz/yd$^2$). A second layer was formed of 60% polyester (SD-10 manufactured by Sam Yang having offices in Seoul, South Korea) and 40% PP-196 polypropylene by blending on a conventional carding machine. The second layer had a basis weight of about 32 g/m$^2$ (0.9 oz/yd$^2$). The first and second layers were thermobonded together by heated bonding rolls as shown in FIGS. 3 and 3a., with the bonding roll contacting the first layer maintained at a temperature of about 272° F. (133° C.) and the bonding roll contacting the second layer maintained at a temperature of about 315° F. (157° C.) The line speed for the bonding rolls was about 80 ft/min. (24 m/min.) and the nip pressure between the bonding rolls was about 300 pli. The thermobonding process yielded a nonwoven laminated material having a spaced apart bonding pattern with apertures formed within the bonding regions and a percent bond area of about 2%.

Example 2

A first layer was formed of 100% PP-196 polypropylene by blending on a conventional carding machine as described above. The first layer had a basis weight of about 18 g/m$^2$ (0.5 oz/yd$^2$). A second layer was formed of 60% polyester (PET-295 manufactured by Hoechst Celanese having offices in Greenville, S.C.) and 40% PP-196 polypropylene by blending on a conventional carding machine. The second layer had a basis weight of about 32 g/m$^2$ (0.9 oz/yd$^2$). The first and second layers were thermobonded together by heated bonding rolls as shown in FIGS. 3 and 3a., with the bonding roll contacting the first layer maintained at a temperature of about 272° F. (133° C.) and the bonding roll contacting the second layer maintained at a temperature of about 315° F. (157° C.) The line speed for the bonding rolls was about 80 ft/min. (24 m/min.) and the nip pressure between the bonding rolls was about 300 pli. The thermobonding process yielded a nonwoven laminated material having a spaced apart bonding pattern with apertures formed within the bonding regions and a percent bond area of about 2%.

Example 3

A first layer was formed of 100% polypropylene fibers (PT110–20 supplied by Lohmann GmbH & Co. KG having offices in Neuwied, Germany). The first layer had a basis weight of about 20 g/m$^2$ (0.5 oz/yd$^2$). A second layer was formed of 60% polyester (PET-292 manufactured by Hoechst/AG having offices in Frankfurt, Germany) and 40% polypropylene (PP-71 "SOFT-71" manufactured by Danaklon A/S, Inc. having offices in Varde, Denmark) by blending on a conventional carding machine as described above. The second layer had a basis weight of about 32 g/m$^2$ (0.9 oz/yd$^2$). The first and second layer were thermobonded together by heated bonding rolls as shown in FIGS. 3 and 3a., with the bonding roll contacting the first layer maintained at a temperature of about 272° F. (133° C.) and the bonding roll contacting the second layer maintained at a temperature of about 315° F. (157° C.) The line speed for the bonding rolls was about 80 ft/min. (24 m/min.) and the nip pressure between the bonding rolls was about 300 pli. The thermobonding process yielded a nonwoven laminated material having a spaced apart bonding pattern with apertures formed within the bonding regions and a percent bond area of about 2%.

Example 4

A first layer was formed of 100% PP-71 polypropylene using a conventional spunbonding forming process. The first layer had a basis weight of about 22 g/m$^2$ (0.6 oz/yd$^2$). A second layer was formed of 60% polyester PET-292 and 40% PP-71 polypropylene by blending on a conventional carding machine. The second layer had a basis weight of about 32 g/m$^2$ (0.9 oz/yd$^2$). The first and second layer were thermobonded together by heated bonding rolls as shown in FIGS. 3 and 3a., with the bonding roll contacting the first layer maintained at a temperature of about 272° F. (133° C.) and the bonding roll contacting the second layer maintained at a temperature of about 315° F. (157° C.) The line speed for the bonding rolls was about 80 ft/min. (24 m/min.) and the nip pressure between the bonding rolls was about 300 pli. The thermobonding process yielded a nonwoven laminated material having a spaced apart bonding pattern with apertures formed within the bonding regions and a percent bond area of about 2%.

Example 5

A first layer was formed of 100% polypropylene (75% PP-196 and 25% PP-190, both manufactured by Hercules, Inc. having offices in Wilmington, Del.) by blending on a conventional carding machine as described above. The first layer had a basis weight of about 18 g/m$^2$ (0.5 oz/yd$^2$). A second layer was formed of 60% PET-292 polyester and 40% PP-71 polypropylene by blending on a conventional carding machine. The second layer had a basis weight of about 32 g/m² (0.9 oz/yd²). The first and second layer were thermobonded together by heated bonding rolls as shown in FIGS. 3 and 3a., with the bonding roll contacting the first layer maintained at a temperature of about 272° F. (133° C.) and the bonding roll contacting the second layer maintained at a temperature of about 315° F. (157° C.) The line speed for the bonding rolls was about 80 ft/min. (24 m/min.) and the nip pressure between the bonding rolls was about 300 pli. The thermobonding process yielded a nonwoven laminated material having a spaced apart bonding pattern with apertures formed within the bonding regions and a percent bond area of about 2%.

Example 6

A first layer was formed of 100% PP-196 polypropylene by blending on a conventional carding machine as described above. The first layer had a basis weight of about 18 g/m² (0.5 oz/yd²). A second layer was formed of 60% PET-295 polyester and 40% PP-196 polypropylene by blending on a conventional carding machine. The second layer had a basis weight of about 32 g/m² (0.9 oz/yd²). The first and second layers were thermobonded together by heated bonding rolls as shown in FIGS. 3 and 3a., with the bonding roll contacting the first layer maintained at a temperature of about 272° F. (133° C.) and the bonding roll contacting the second layer maintained at a temperature of about 315° F. (157° C.) The line speed for the bonding rolls was about 80 ft/min. (24 m/min.) and the nip pressure between the bonding rolls was about 300 pli. The thermobonding process yielded a nonwoven laminated material having a spaced apart bonding pattern with apertures formed within the bonding regions and a percent bond area of about 2%.

The resultant nonwoven laminated materials of the above examples had the properties set forth in the following table:

TABLE I

| Example | Basis Weight (g/m²) | Thickness (in.) | Density (g/cc) | Tensile (g/in.) MD | Tensile (g/in.) CD | % Elongation MD |
|---|---|---|---|---|---|---|
| 1 | 49.0 | 0.046 | 0.041 | 1578.0 | 196.0 | 33.2 |
| 2 | 52.0 | 0.046 | 0.044 | 1585.0 | 198.0 | 32.0 |
| 3 | 51.0 | 0.048 | 0.042 | 2672.0 | 402.0 | 29.2 |
| 4 | 56.5 | 0.051 | 0.043 | 1439.0 | 382.0 | 26.1 |
| 5 | 51.2 | 0.057 | 0.034 | 1509.0 | 228.0 | 39.6 |
| 6 | 51.5 | 0.058 | 0.035 | 1610.0 | 263.0 | 37.3 |

For the purposes of the present disclosure, the following test procedures can be used to determine particular parameters of the nonwoven material 10 of the present invention.

The Fluid Intake and Flowback Evaluation (FIFE) test has been designed to measure the absorbency/penetration time, flowback amount and amount of liquid retention in the liner of a disposable absorbent article. The absorbency/penetration time (in seconds) is measured by using a stopwatch and visually determining the length of time required to absorb simulated urine voidings. The flowback test measures, in grams, the amount of liquid that emerges from the "user side" of the absorbent article after it has absorbed each of three liquid insults and pressure has been applied.

Figure 8:
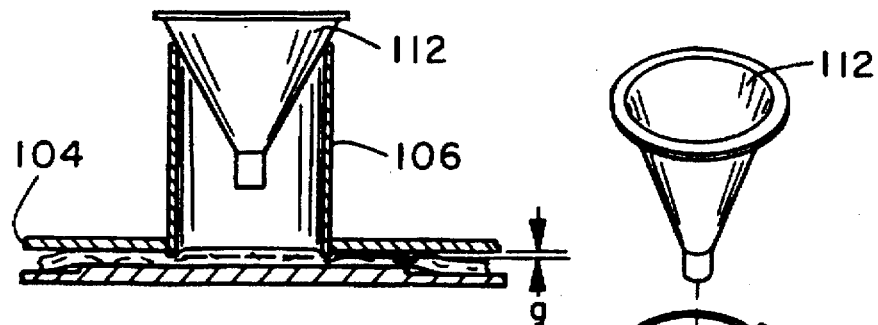
FIG. 8 is a cross-sectional view of FIG. 7.
Figure 7:
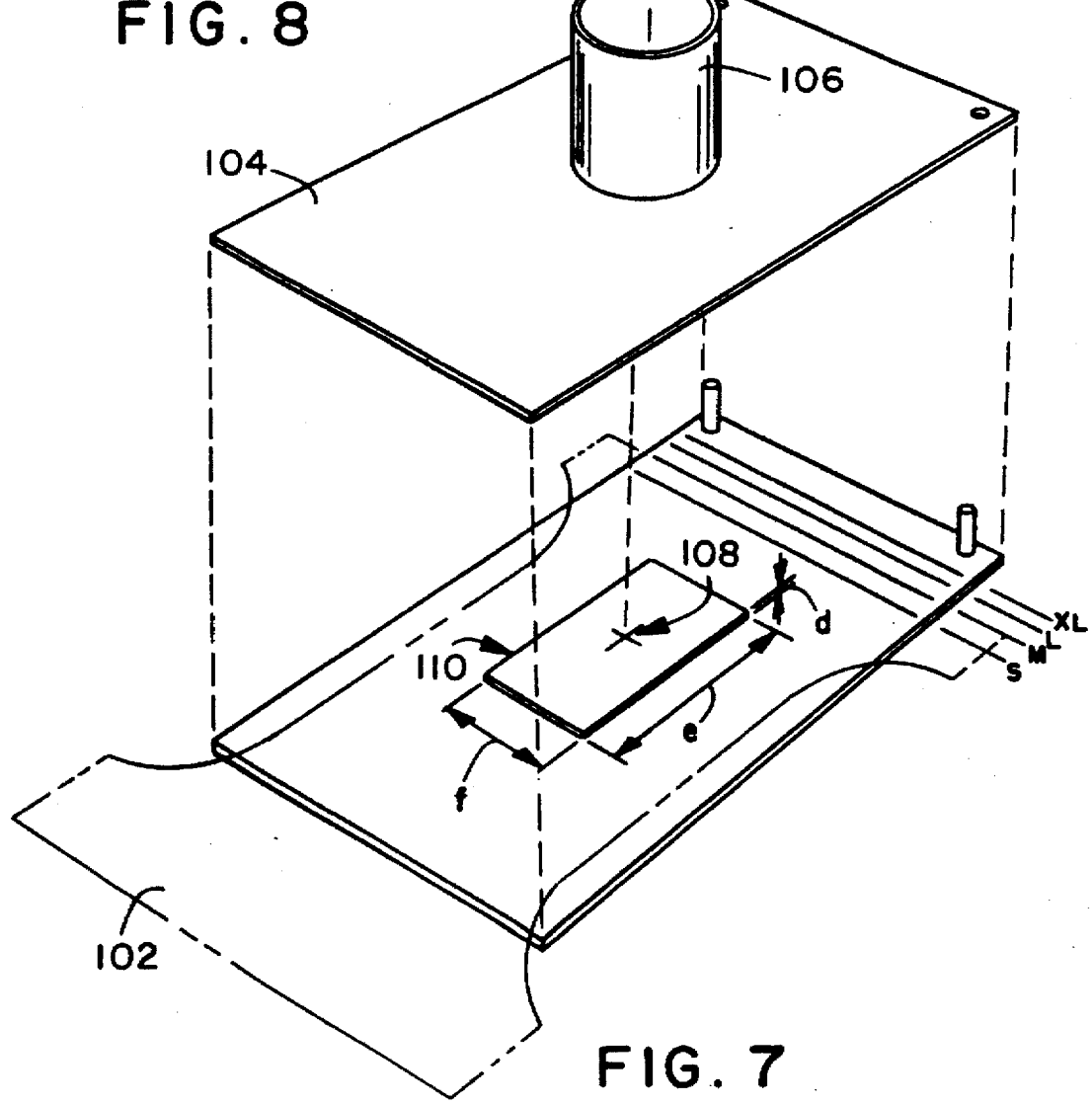
FIG. 7 is a perspective view of a testing apparatus used to evaluate fluid intake and flowback of nonwoven laminated materials of the type described herein.

The apparatus shown in FIGS. 7 and 8 is used for this test. A sample diaper to be tested, as shown in FIG. 4 and shown in phantom at 102 in FIG. 7, is weighed to the nearest 0.1 g. The sample 102 is prepared by cutting the leg and waist elastic members and containment flap elastics (not shown) along their length in order to allow the sample to lie flat.

Sample dimensions, weight and density profiles of the sample 102 and composition of the absorbent core must be appropriately controlled to obtain valid results. Data reported herein were obtained from 12 in.×12 in. (305 mm.×305 mm.) rectangular samples including the nonwoven materials 10 described above in Examples 4, 5 and 6 and absorbent cores containing about 10 grams of woodpulp fluff and about 12 grams of superabsorbent material, such as DOW DRYTECH 835 or an equivalent thereof.

The sample 102 is placed flat and smooth under an 880 g. cylinder plate assembly 104 such that the cylinder 106, which has a 5.1 cm i.d., ends up in a designated location 108. For example, the designated location 108 can range from about 4½ inches (114.3 mm.) to about 5¾ inches (146.1 mm.) from the edge of the sample 102, depending upon the size (e.g., small (s), medium (m), large(l) or extra large(xl)) of the absorbent article to be tested. Under the sample 102 is a raised platform 110 that is ½ inch (12.7 mm.) high (d)×6 inches (152.4 mm.) long (e)×3 inches (76.2 mm.) wide (f). Also, the cylinder 106 extends a distance (g) of about ¹⁄₃₂ inch (0.8 mm.) below the cylinder plate assembly 104.

Funnel 112 on top of cylinder 106 is perpendicular to the sample 102 and centered on the designated location 108. A specified amount of synthetic urine (e.g., 50 ml, 80 ml or 100 ml for small, medium and large or extra large diapers, respectively), is poured through the funnel 112. (An example of a suitable synthetic urine is Item No. K-C 399105, available from PPG Industries having offices in Appleton, Wis.) The time elapsing between the first liquid contact with the sample 102 and the time when liquid no longer is visible on the surface of the sample 102 is measured with a stop watch. One minute after the initial liquid insult is imbibed, a second insult of the same size is introduced. The time to imbibe the second insult of liquid is measured as for the first insult.

Figure 9:
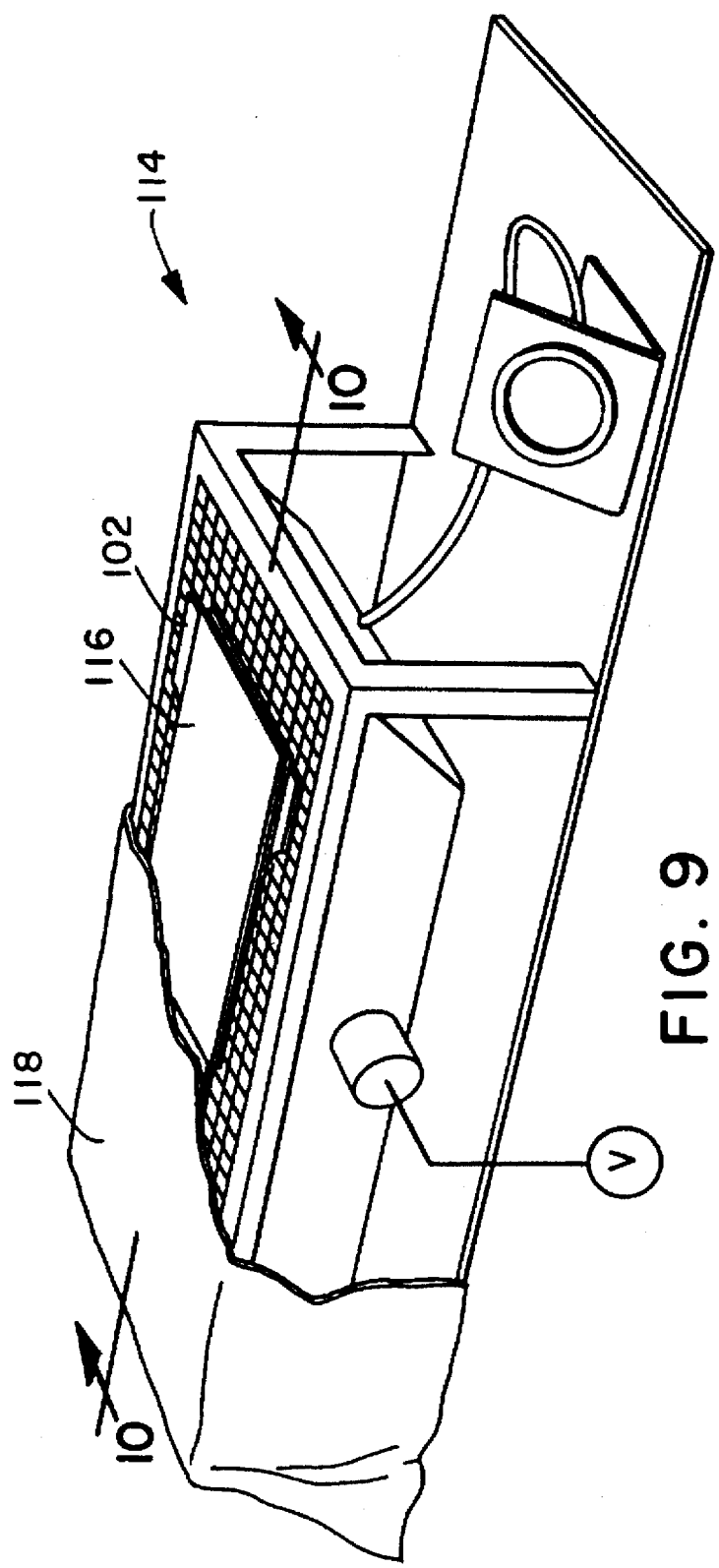
FIG. 9 is a perspective view showing a fluid flowback testing apparatus used to evaluate nonwoven laminated materials of the type described herein.
Figure 10:
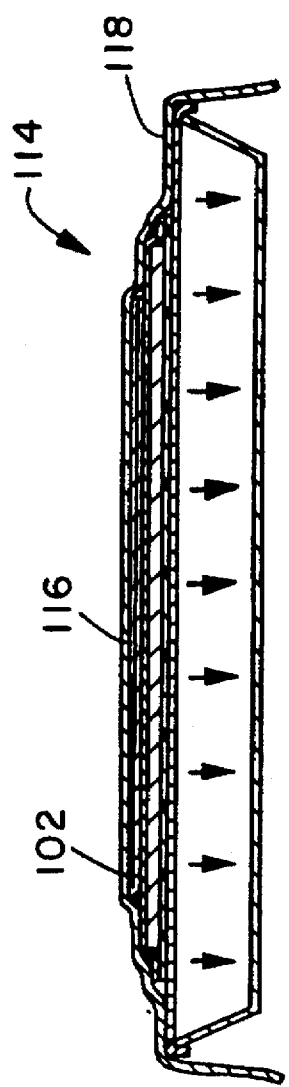
FIG. 10 is a cross-sectional view of FIG. 9.

Referring now to FIGS. 9 and 10, one minute after the second insult is imbibed, the sample 102 is placed on a vacuum apparatus 114 and covered with blotter paper 116 together with liquid impervious latex sheeting 118. A 35,000 dyne/cm² (about 0.5 psi) vacuum pressure then is applied to suck the impervious latex sheeting 118 onto the blotter 116 and sample 102 for two minutes. After the pressure is released, the wet blotter paper 116 then is weighed. The increase in weight (in grams) of the blotter paper 116 represents the flowback.

Within one minute after the pressure is released from the sample 102, a third liquid insult is introduced and timed as described above. The liquid intake time then is the number of seconds for the prescribed amount of liquid (80 ml for the results described herein) to enter the sample 102.

Samples 102 including the nonwoven laminated materials of the above Examples 4, 5 and 6 had the flowback and liquid intake time values set forth in the following table:

TABLE II

| Example | FIFE Liquid Intake Time (seconds) | FIFE Flowback (grams) |
|---|---|---|
| 4 | 33 | 7.1 |
| 5 | 34 | 1.9 |
| 6 | 30 | 3.2 |

While the Fluid Intake and Flowback Evaluation test results are indicated above for several specific Examples, absorbent articles incorporating the nonwoven material 10 described herein can have liquid intake times ranging from about 11 seconds to about 38 seconds and flowback values ranging from about 1.0 gram to about 9.0 grams.

It is contemplated that the nonwoven material 10 constructed in accordance with the present invention will be tailored and adjusted by those of ordinary skill in the art to accommodate various levels of performance demand imparted during actual use. For example, mild urinary incontinence and menstrual flow pads involve different delivery rates, volumes and timing than infant urine insults. Moreover, the liquid in the surge can vary in terms of the liquid viscosity, surface tension, temperature and other physical properties that could affect the performance of the nonwoven material 10 in the various actual product end usages. Accordingly, while this invention has been described by reference to the above embodiments and examples, it will be understood that this invention is capable of further modifications. This application is, therefore, intended to cover any variations, uses or adaptations of the invention following the general principles thereof, and including such departures from the present disclosure as come within known or customary practice in the art to which this invention pertains and fall within the limits of the appended claims.

I claim:

1. An apparatus for forming a laminated fibrous material comprising:

means for providing a fibrous layer comprising a plurality of fibers or filaments of one or more thermoplastic polymeric materials;

means for providing a second fibrous layer comprising a plurality of fibers or filaments of two or more thermoplastic polymeric materials;

means for bonding said first and second layers at an interface between said layers in a spaced apart bonding pattern comprising compacted bonding regions having a first degree of bonding separated by second, lesser bonded fiber spans;

said bonding means comprising a first thermal bonding roll and a second thermal bonding roll opposedly positioned relative to each other, each of said bonding rolls having an outer surface in contact with one of said first and second layers of said first and second layers passing therebetween, said first and second bonding rolls having different raised bonding patterns on said outer surfaces thereof, said first bonding roll having a spaced apart raised bonding pattern on the outer surface thereof and said second bonding roll having a plurality of raised bonding points on the outer surface thereof;

means for operating said first bonding roll at a first rotational speed and means for operating said second bonding roll at a second rotational speed, said operating means ensuring that said first and second rotational speeds differ within a range of from about 4 percent to about 50 percent;

means for maintaining said first bonding roll at a first bonding temperature within the range of from about 260° F. to about 285° F. and means for maintaining said second bonding roll at a second bonding temperature within the range of from about 270° F. to about 320° F., said maintaining means maintaining said first and second bonding rolls at different bonding temperatures; and said bonding rolls forming apertures within said bonding regions, said apertures being substantially free of fibers through the thickness of said laminated fibrous material.

2. An apparatus for forming a laminated fibrous material according to claim 1 further comprising first bonding means for bonding fibers of said first fibrous layer to one another.

3. An apparatus for forming a laminated fibrous material according to claim 1 wherein the formation of said apertures is substantially limited to said bonding regions.

4. An apparatus for forming a laminated fibrous material according to claim 1 wherein said bonding means bonds said first and second layers together in a spaced apart bonding pattern such that the resulting laminated fibrous material has a percent bond area of from about 1% to about 6%.

5. An apparatus for forming a laminated fibrous material according to claim 1 wherein said spaced apart bonding pattern is formed by points of contact between said raised bonding patterns on said outer surfaces of said first and second bonding rolls.

6. An apparatus for forming a laminated fibrous material according to claim 5 wherein said apertures are formed by points of contact between said raised bonding patterns on said outer surfaces of said first and second bonding rolls.

7. An apparatus for forming a laminated fibrous material according to claim 1 wherein said first bonding roll has a percent bond area of from about 9 percent to about 20 percent and said second roll has a percent bond area of from about 10 percent to about 30 percent.

8. An apparatus for forming a laminated fibrous material according to claim 1 wherein said raised bonding patterns of said first and second bonding rolls are configured to optimize the number of said apertures formed within said bonding regions.

9. An apparatus for forming a laminated fibrous material according to claim 1 wherein said first bonding temperature ranges from about 265° F. to about 275° F. and said second bonding temperature ranges from about 290° F. to about 315° F.

10. An apparatus for forming a laminated fibrous material according to claim 1 wherein said first fibrous layer contacts said first bonding roll and said second fibrous layer contacts said second bonding roll during rotation and heating of said rolls.

11. An apparatus for forming a laminated fibrous material according to claim 1 wherein said operating means rotate said first and second bonding rolls such that said first and second fibrous layers passing therebetween have a line speed ranging from about 20 meters per minute to about 100 meters per minute.

12. An apparatus for forming a fibrous material according to claim 1 further comprising means for producing a nip pressure of from about 60 pounds per linear inch to about 400 pounds per linear inch within a nip formed between said first and second bonding rolls.

* * * * *